United States Patent [19]

Pruitt

[11] Patent Number: 4,930,503

[45] Date of Patent: Jun. 5, 1990

[54] STAPLING PROCESS AND DEVICE FOR USE ON THE MESENTERIES OF THE ABDOMEN

[76] Inventor: J. Crayton Pruitt, 360 Coffee Pot Riviera NE., St. Petersburg, Fla. 33704

[21] Appl. No.: 350,758

[22] Filed: May 12, 1989

Related U.S. Application Data

[63] Continuation-in-part of Ser. No. 237,433, Aug. 26, 1988, Pat. No. 4,848,637, which is a continuation-in-part of Ser. No. 60,469, Jun. 11, 1987, abandoned, which is a continuation-in-part of Ser. No. 864,336, May 19, 1986, abandoned.

[51] Int. Cl.[5] .................... A61B 17/04; B31B 1/00
[52] U.S. Cl. ..................................... 227/178; 227/19
[58] Field of Search ............. 128/334 R; 227/DIG. 1, 227/19

[56] References Cited

U.S. PATENT DOCUMENTS

| | | | |
|---|---|---|---|
| 3,252,643 | 5/1966 | Strekopytov et al. | 227/DIG. 1 |
| 3,275,211 | 9/1966 | Hirsch et al. | 227/DIG. 1 |
| 3,494,533 | 2/1970 | Green et al. | 227/DIG. 1 |
| 3,795,034 | 3/1974 | Strekopytov et al. | 227/DIG. 1 |
| 3,958,738 | 5/1976 | Tremblay | 227/109 |
| 4,383,634 | 5/1983 | Green | 227/DIG. 1 |
| 4,520,817 | 6/1985 | Green | 227/DIG. 1 |
| 4,606,345 | 8/1986 | Dorband et al. | 227/DIG. 1 |
| 4,667,865 | 5/1987 | Judge | 227/109 |
| 4,715,520 | 12/1987 | Roehr et al. | 128/334 R |
| 4,802,614 | 2/1989 | Green et al. | 227/19 |

Primary Examiner—Edward M. Coven
Assistant Examiner—Gary Jackson
Attorney, Agent, or Firm—Walter J. Monacelli

[57] ABSTRACT

The stapling processes described herein comprise those suitable for stapling a patient's mesentery and omentum with three or four rows of staples being substantially parallel to each other and the staples in one row being staggered with staples of the same size in another row, there being at least one row in which the staples differ in size from the staples in the other rows. Advantageously the larger staples are 30–50 percent larger, preferably about 33 percent larger than the smaller staples. Also advantageously the smaller staples are similar to those presently used as vascular staples, in the range of 2.5–3.5 mm, preferably about 3 mm, and the larger staples are advantageously in the range of 3.5–4.5 mm, preferably about 4 mm. This arrangement is capable of satisfactorily sealing off the variety of sizes of blood vessels and holding firmly the fatty tissue found in the mesentery and in the omentum. Other arrangements of staples have been designated to effect similar results in the mesentery in which the smaller and larger staples are arranged alternately in the same row so that the gaps between staples are covered by staples staggered therewith in an adjacent row of staples.

28 Claims, 12 Drawing Sheets

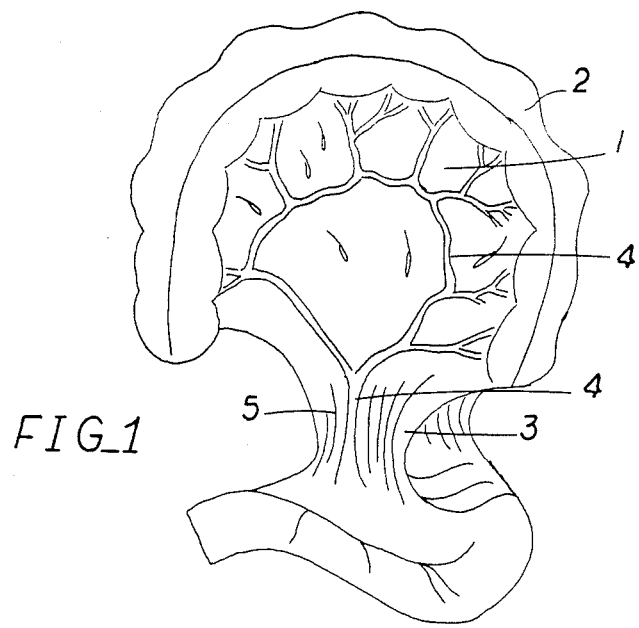
FIG_1
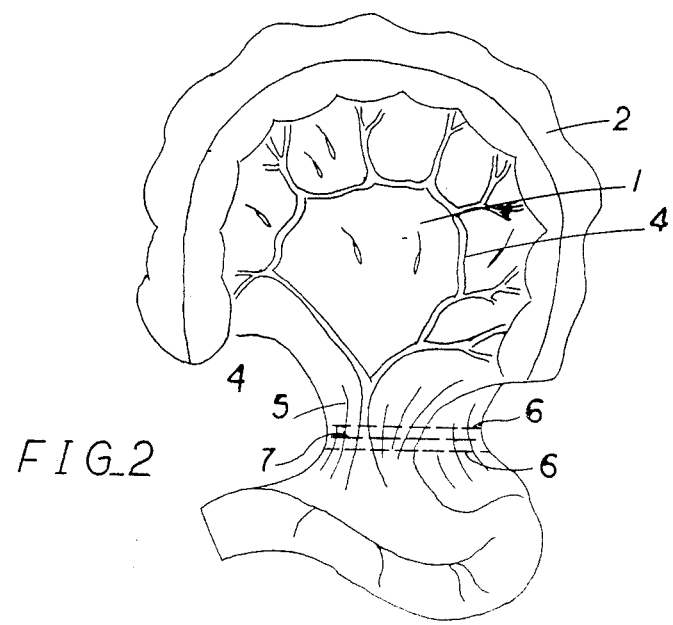
FIG_2

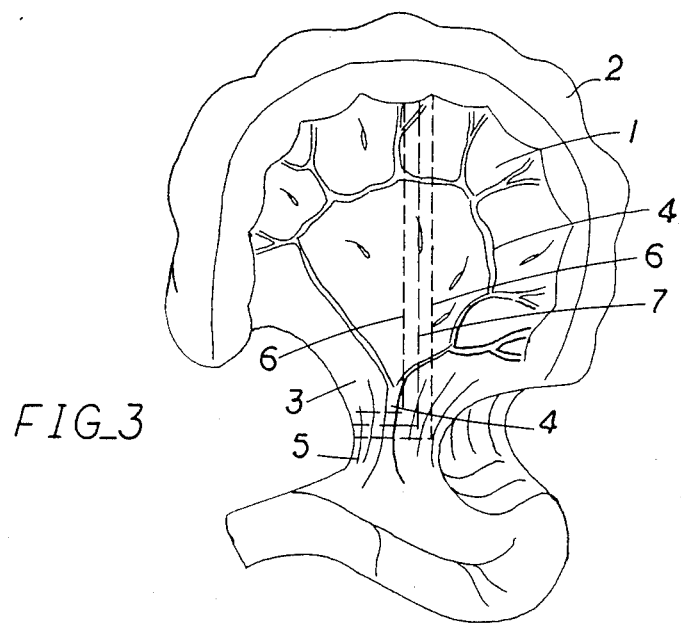
FIG_3
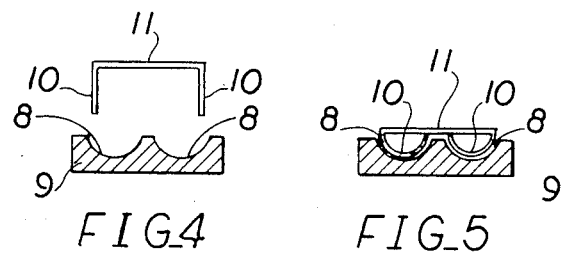
FIG_4    FIG_5
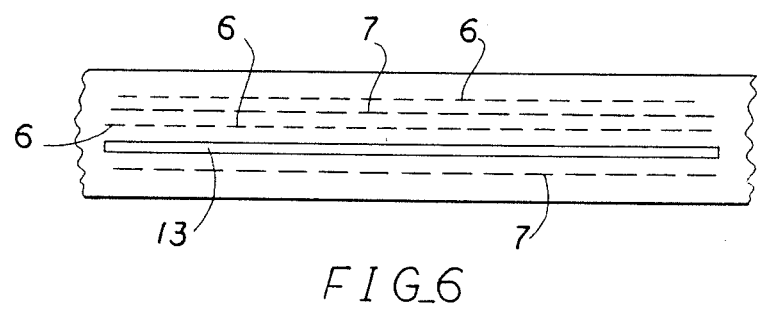
FIG_6

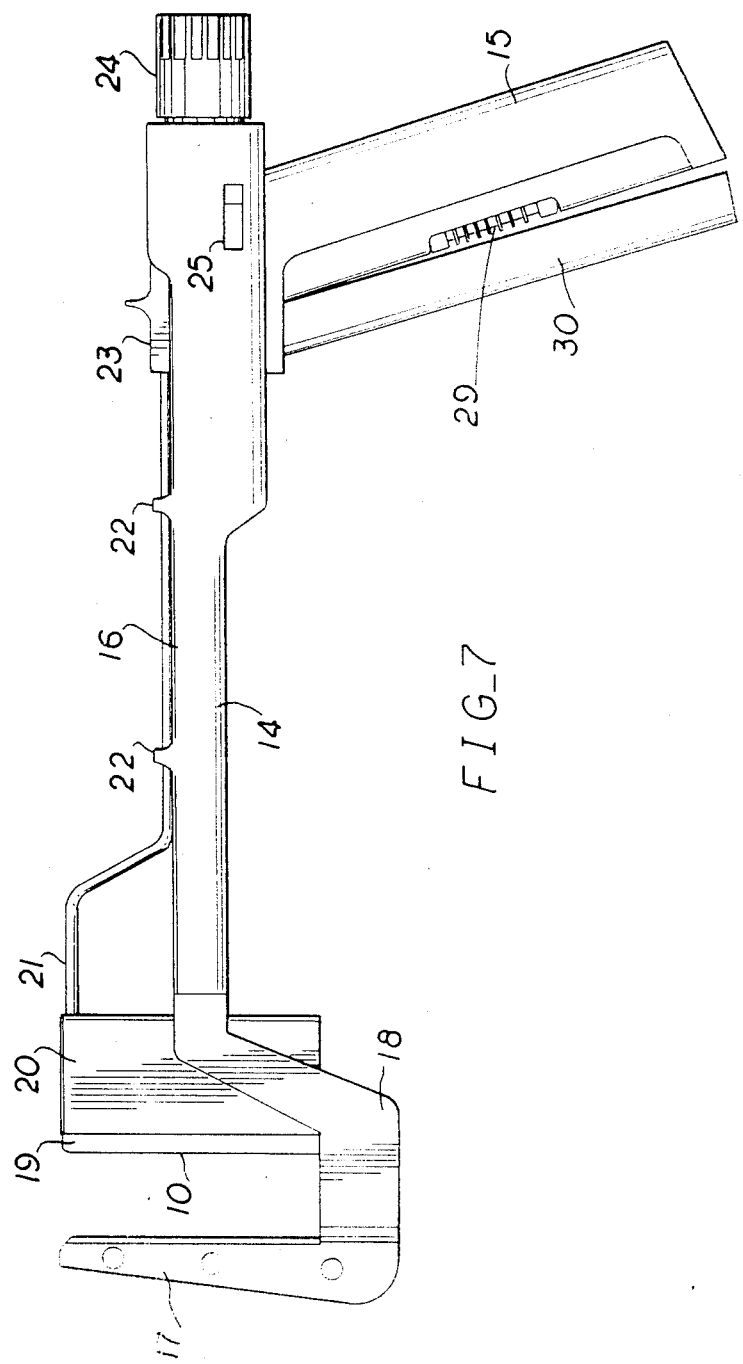
FIG_7

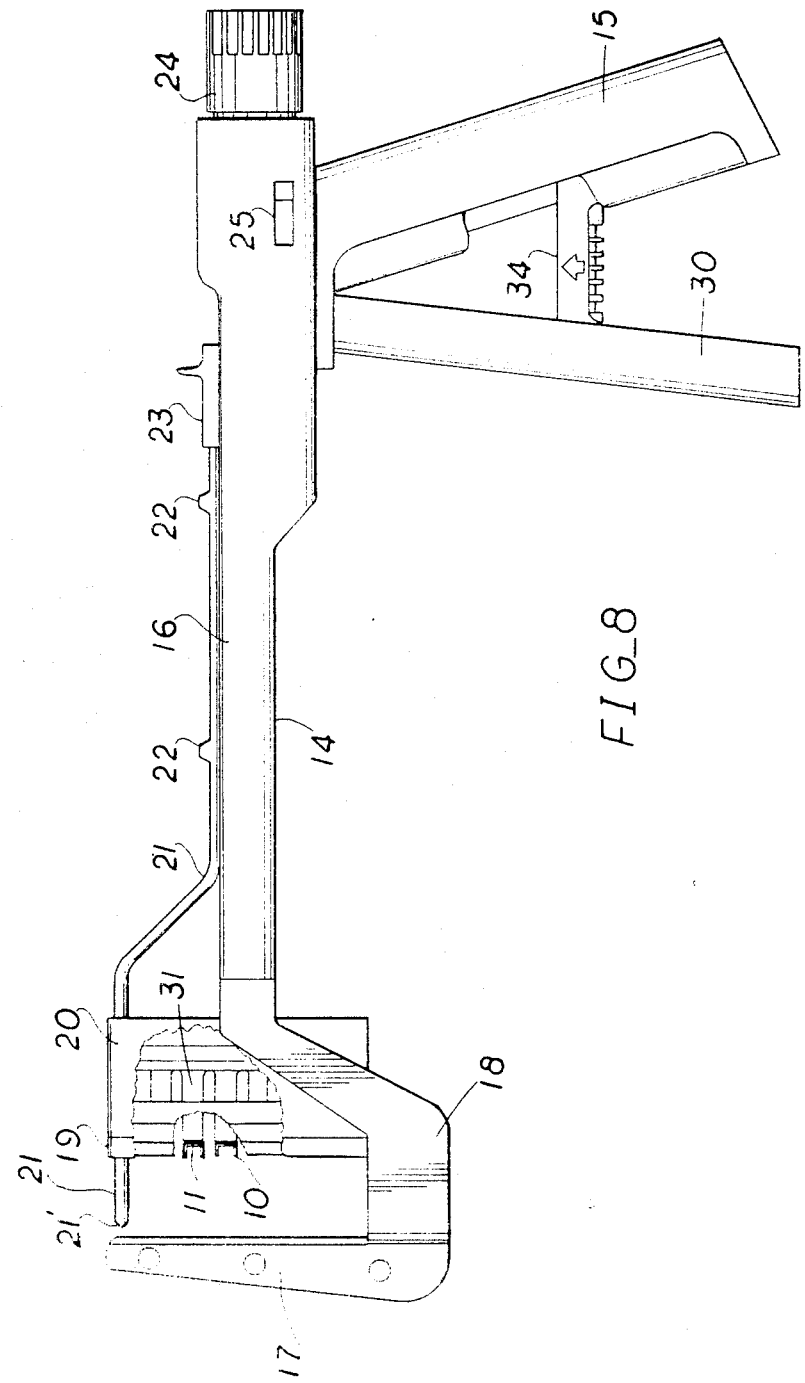

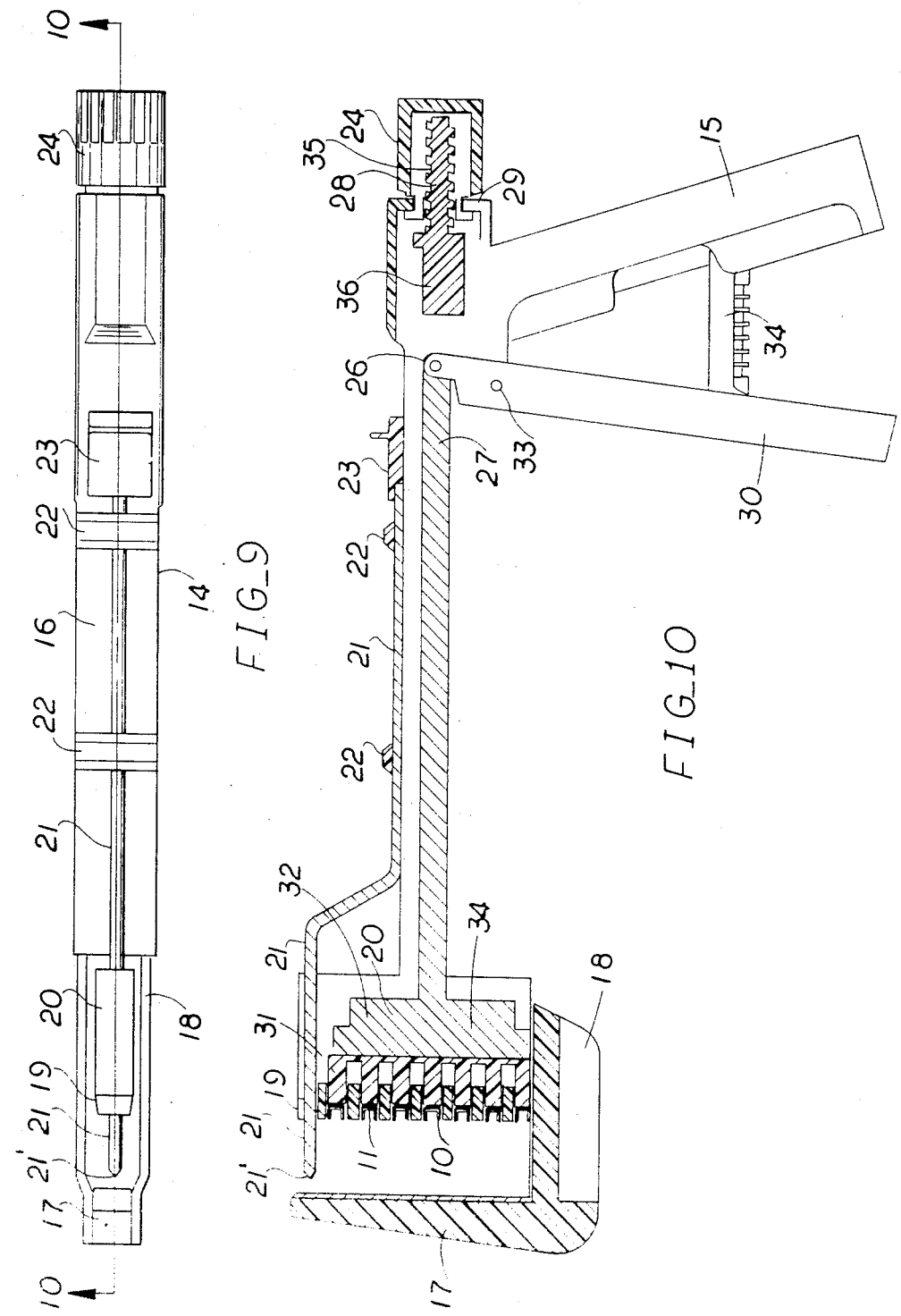

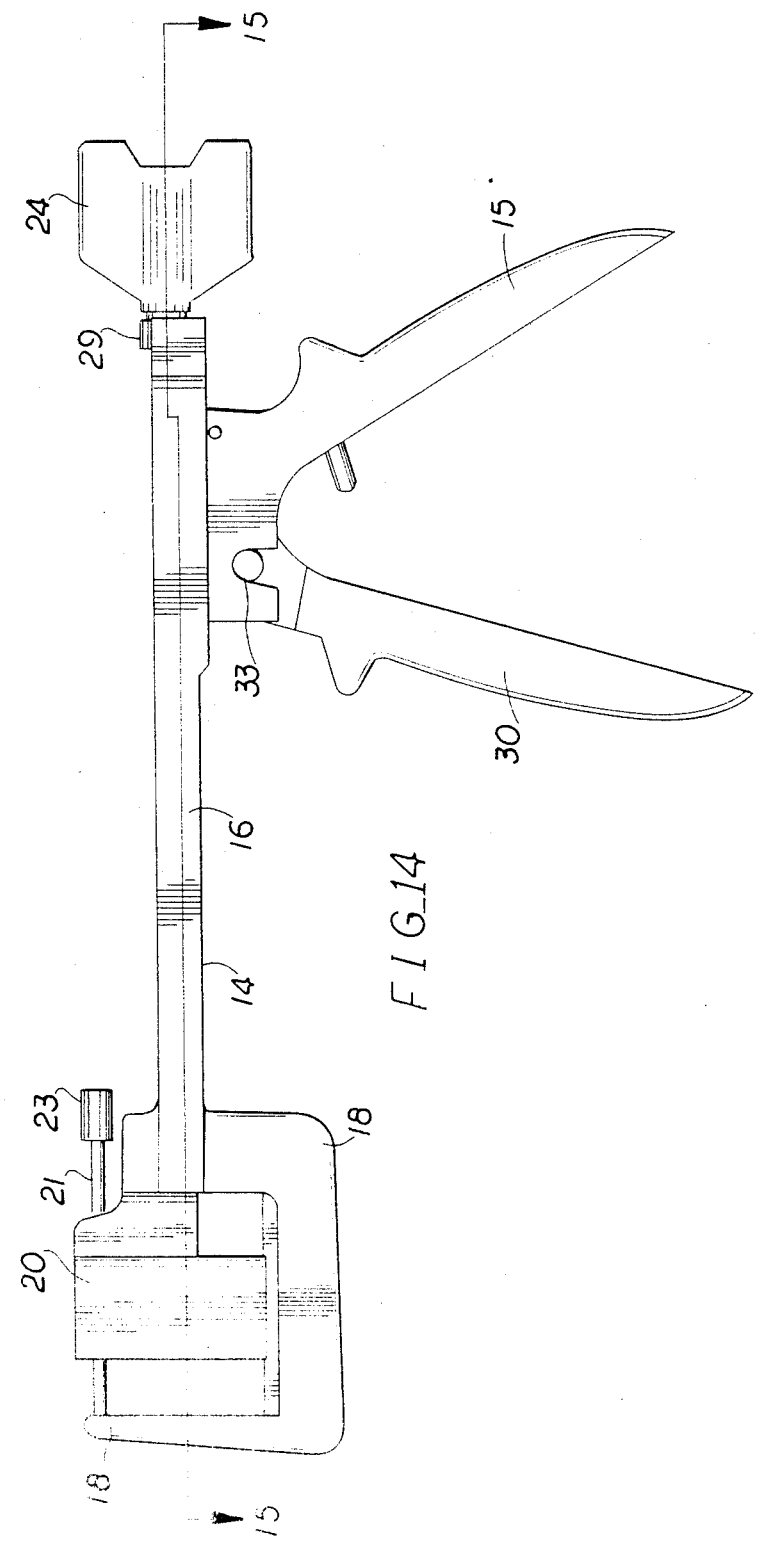

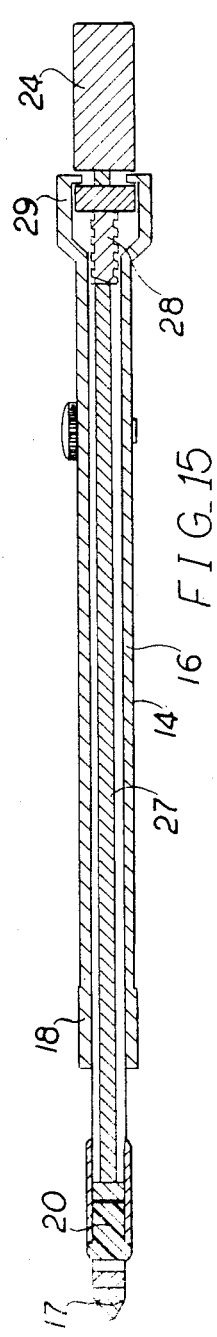
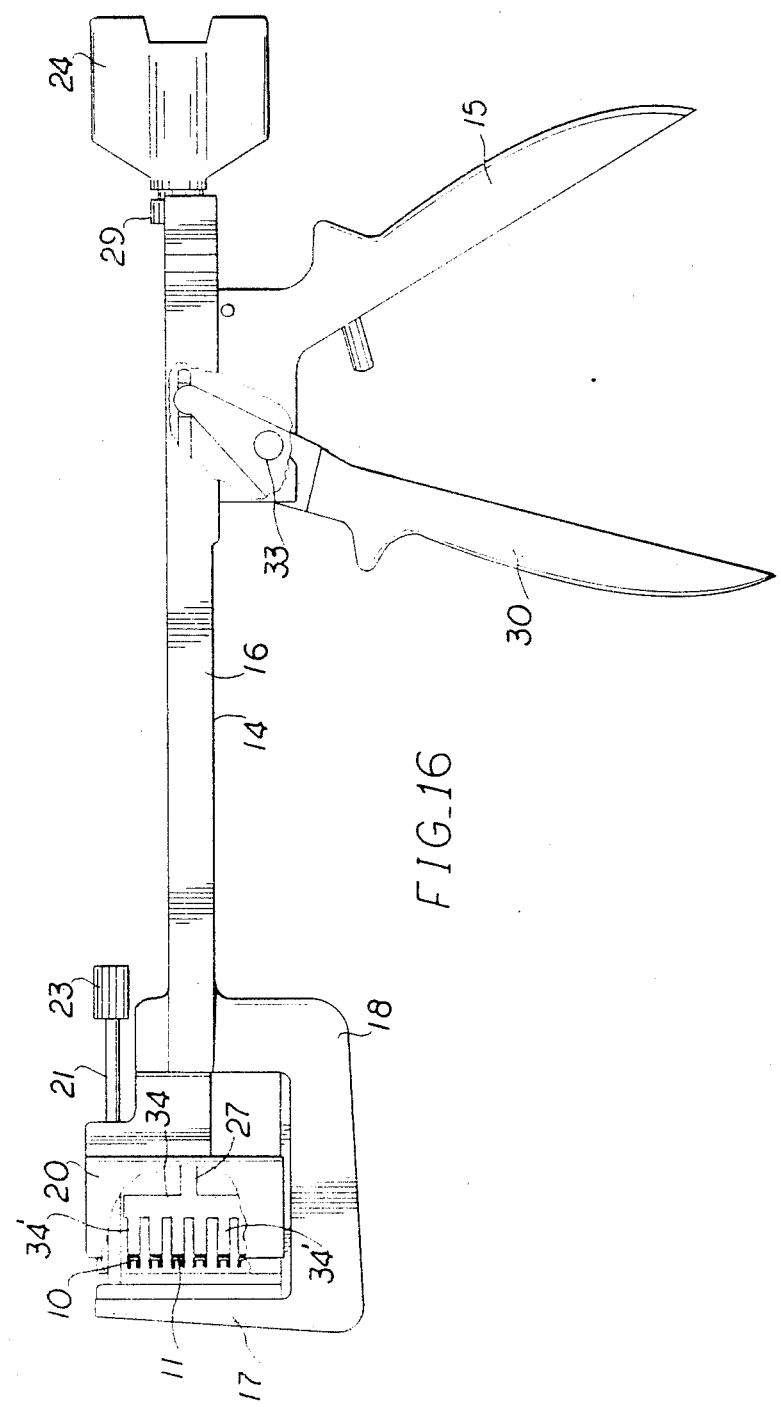

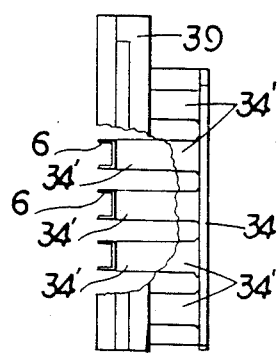
FIG_17
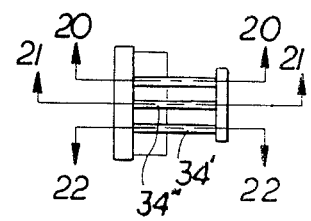
FIG_18
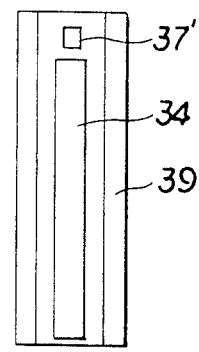
FIG_19
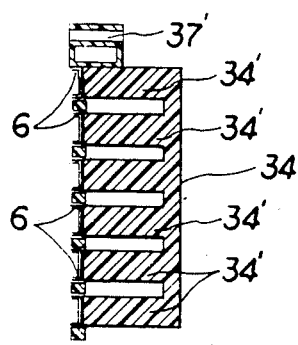
FIG_20
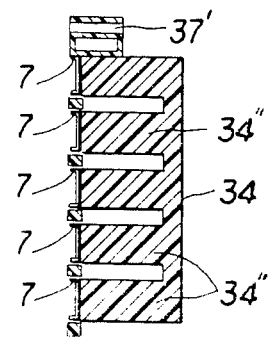
FIG_21
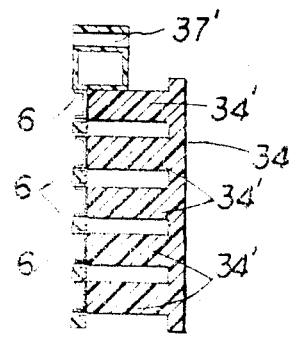
FIG_22

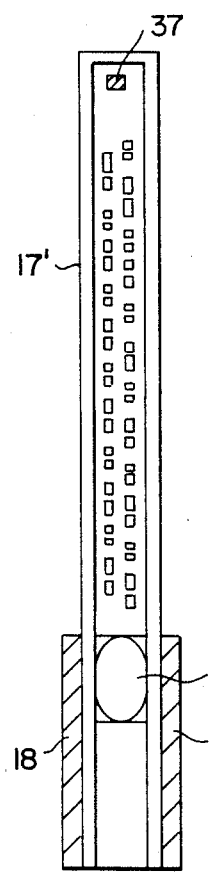 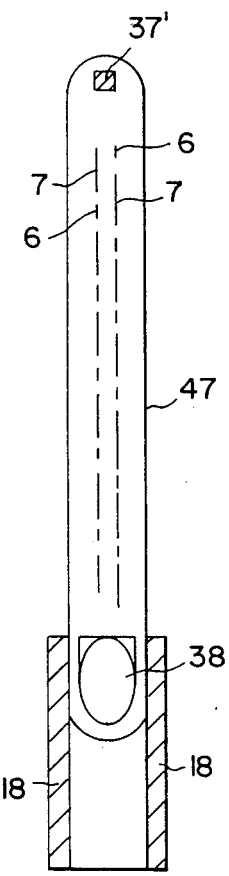 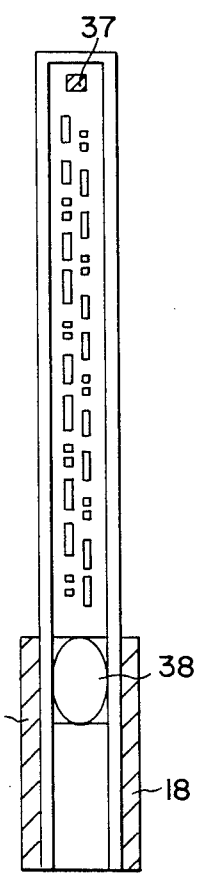 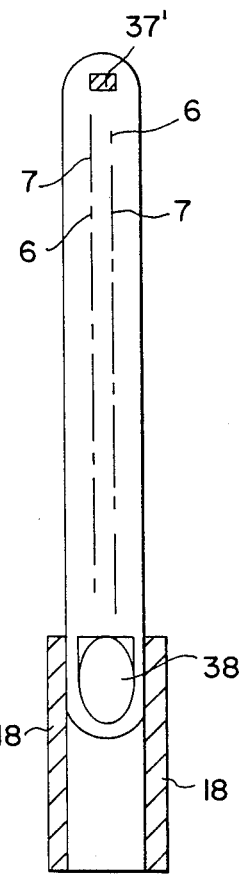
FIG. 39   FIG. 40   FIG. 41   FIG. 42
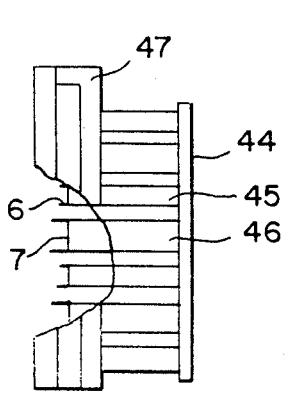 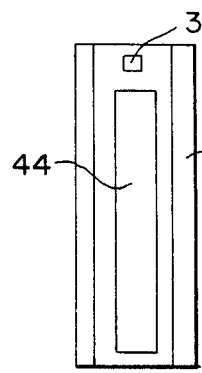 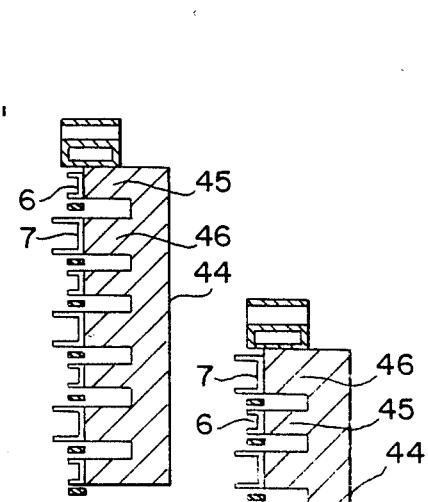
FIG. 43   FIG. 45   FIG. 46
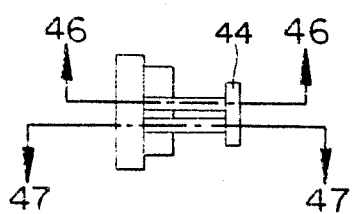 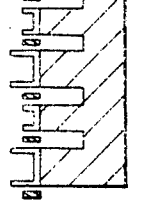
FIG. 44   FIG. 47

STAPLING PROCESS AND DEVICE FOR USE ON THE MESENTERIES OF THE ABDOMEN

This application is a continuation-in-part of copending application Ser. No. 07/237,433, filed Aug. 26, 1988, issued on Jul. 18, 1989 as U.S. Pat. No. 4,848,637, which in turn is a continuation-in-part of application Ser. No. 07/060,469, filed Jun. 11, 1987, now abandoned, which in turn is a continuation-in-part of Ser. No. 06/864,336 filed May 19, 1986, now abandoned.

FIELD OF THE INVENTION

This invention relates to a process for stapling the mesenteries of a patient's abdomen. More specifically this invention relates to a process for use in the mesenteries of a patient's abdomen. Still more specifically it relates to a process of applying three or four rows of staples with at least one row varying in staple size from the size of staples in the other rows and designed to be applied to the fatty tissue of the mesenteries so as to seal off the blood vessels of varying size therein. It relates specifically to similar results from two or three rows of staples in which large and small staples are positioned alternately in each row of staples.

BACKGROUND OF THE INVENTION

The stomach, appendix, jejunum, ileum, ascending colon, transverse colon, descending colon, liver and spleen are attached to the posterior part of the abdominal wall by mesenteries which carry blood vessels and lymphatics to and from these organs. The mesenteries also contain lymph nodes. The mesenteries vary in thickness, but all contain large amounts of fatty tissue and blood vessels which vary in size from 1.0 cm. in diameter down to less than 0.1 mm. in diameter. The greater omentum is a double fold of mesentery and it too carries large numbers of blood vessels of varying size, and the thickness of the greater omentum is quite variable from one patient to another.

There are stapling devices for closing the bronchus, pulmonary artery, pulmonary veins, for closure of the large or small intestine, for closure of the stomach or stapling of the stomach for morbid obesity, for end-to-end anastomosis of the intestines, for side-to-side anastomosis of the intestines and for individual ligation and for division of a blood vessel. In addition, there is a variety of occluding clips for blood vessels and skin staplers. Because of the fatty tissue and the variety of sizes of blood vessels present in the mesentery and the omentum, the available staplers are not satisfactory for stapling the mesentery and the omentum. The best stapler only ligates one vessel at a time and it commonly tears blood vessels in the vicinity of its use, requiring time-consuming repairs after ligation of the intended vessel.

U.S. Pat. Nos. 4,606,345 (Dorband et al), 3,252,643 (Strekopytov et al), 3,795,034 (Strekopytov et al), Roehr et al 4,715,520, Tremblay 3,958,738 and Judge 4,667,865 were cited against the parent applications.

The Dorband et al patent describes a stapler gun and a method for stapling two staggered rows of two-part fasteners for joining body tissue with two-part plastic fasteners which are believed to be more suitable for remaining in the patient as compared to stainless steel staples. The device is designed to provide two rows of fasteners, which fasteners may be made of biologically absorable or non-absorbable polymeric materials. One part of the fastener comprises a U-shaped staple which has legs that are caused to penetrate the tissue. The other part of the fastener is placed on the other side of the tissue and used to engage the legs of the staple and interlock therewith. There is no disclosure of three rows of fastening devices, nor is there any disclosure of variations in the size of the fasteners, nor is there any discussion of this arrangement being satisfactory for use with a patient's mesentery.

The Strekopytov U.S. Pat. Nos. (3,252,643 and 3,795,034) teach an older type of device used for applying rows of staples. While both patents teach the use of a third row of staples, this third row is spaced a considerable distance from the first two rows of staples and is "adjacent the opposite side edge of the jaw" of the stapler. Therefore because of this distance the third row does not act in conjunction with the first two rows of staples but merely provides a separate single row of staples. Moreover there is no reference to any differences in sizes of the staples in any of the rows.

The Roehr et al patent shows a stapler which applies three rows of staggered staples. However the staples in each row are identical in size to the staples in the other rows. There is no reference to any variation in the size of the staples.

OBJECTIVES OF THIS INVENTION

It is an objective of this invention to provide a process for effectively stapling the mesentery and the omentum.

It is an objective of this invention to provide a stapler and a cartridge therefor which is suitable for stapling the mesentery and the omentum.

It is also an objective of this invention to provide a stapling process and device with appropriate sizes and arrangement of staples which will satisfactorily seal off blood vessels of varing sizes as found in the mesentery and in the omentum.

SUMMARY OF THE INVENTION

In accordance with the present invention a new process, a new stapler and a new staple cartridge have been designed suitable for use on the mesentery and on the omentum, the use of which process, stapler and cartridge are capable of effectively stopping the bleeding of blood vessels in that part of the mesentery or of the omentum which is being resected. These are designed to apply three or four rows of staples, the rows being substantially parallel to each other and there being at least one row in which the size of the staples differs in size from the size of the staples in other rows. Moreover where adjacent rows have staples of the same size the staples in one such row are staggered from the staples in the adjacent row or rows. Advantageously the larger staples are 30–50 percent larger, preferably about 33 percent larger than the smaller staples. Also advantageously the smaller staples are similar to those presently used as vascular staples in the range of 2.5–3.5 mm, preferably about 3 mm, and the larger staples are advantageously in the range of 3.5–4.5 mm, preferably about 4 mm.

The staple dimensions given above apply to the length of the main part of the staple before being applied or stapled. For example, vascular staples are available commercially with the designation "3.0 mm×2.5 mm (0.118"×0.098")" before closure. The 2.5 mm designation applies to the length of the individual prongs and the 3.0 mm applies to the length of the main body part of the staple. Similarly a larger staple is available with the designation "4.0 mm×4.5 mm (0.157"×0.177")" before closure. Here the prong length is 4.5 mm and the length of the main body portion before closure is 4.0 mm.

Where the stapler or cartridge of this invention is not available, the process of applying staples to the mesentery or omentum may be effected by two staplers, one capable of applying staples of the smaller size is two adjacent, parallel, staggered rows and the other capable of applying staples of the larger size in two adjacent, parallel, staggered rows. The two double rows are applied adjacent to each other and approximately parallel to each other. Where a stapler and a cartridge are available which applies a single row of staples, this may be used in combination with a stapler capable of applying a double row of staples of the opposite size so as to provide in this manner a three row combination in accordance with the practice of this invention.

Where the stapler and cartridges of this invention are available, the three row or four row combinations of staples are preferably applied in that manner.

With the arrangement of parallel adjacent rows of staples of varying size described herein, it is possible to staple the mesentery or omentum to stop bleeding from blood vessels as large as 1.0 cm. in diameter down to blood vessels as small as 0.1 mm. in diameter. Moreover these arrangements of staples are found to resist tearing of the fatty tissue of the mesentery and of the omentum. In one modification of the stapler of this invention a cartridge may be used which provides three rows of staples as described above. In another modification of the stapler of this invention a cartridge may be used which provides four rows of staples as described above.

In the stapler of this invention a cartridge containing the staples of described size and arrangement is inserted in the cartridge holder which is opposite and parallel to the anvil portion of the device. The anvil portion has a number of grooves of appropriate size and slope to bend the prongs or the initially perpendicular portions of the staples as they are thrust through the tissue and into the grooves of the anvil whereby the prongs of the staples are turned inward and toward the main portion of the staple. With continued pressure on the stapler, the ends of the staple are pressed against the main portion of the staple with the fatty tissue and the blood vessels pressed in between. Preferably the prongs of the staple when turned back toward the main part of the staple are curved with the ends of the prongs touching or coming into close proximity to the main part of the staple. This curved structure resembles stitching and avoids squeezing the tissue between the prongs and the main part of the staple as would be the case if the prongs were pressed flush against the main part of staple. This reduces the possibility of having the staple cut through the tissue.

SPECIFIC DESCRIPTION OF THE INVENTION

The description of the stapler and the staple cartridge is simplified by reference to the drawings.

FIG. 1 is a front view of a mesentery and the bowel connected thereto.

FIG. 2 is a similar view as in FIG. 1 with a row of staples across the web or narrow portion of the mesentery.

FIG. 3 is a similar view as in FIG. 1 with a row of staples halfway across the web and another row of staples continuing vertically upward from the first row and extending to the bowel.

FIG. 4 is a side, elevational view of a staple positioned above a groove in the anvil with the anvil portion shown in cross-section taken by a plane coincident with and extending down from the front surface of the staple.

FIG. 5 is a view similar to that of FIG. 4 after the prongs of the staple have been pressed downward into the grooves of the anvil.

FIG. 6 is a top view of a stapled portion of the mesentery in which an extra row of large staples has been positioned parallel to and spaced from the three rows of staples described above.

FIG. 7 is a front elevational view of a preferred modification of the stapler of this invention with the staple cartridge portion at its maximum distance from the anvil.

FIG. 8 is a front elevational view similar to that of FIG. 7 with the positioning rod shown advanced to a position closer to the anvil holding portion and the trigger in an open position.

FIG. 9 is a top view of the stapler shown in FIG. 8.

FIG. 10 is an elevational cross-sectional view taken at line 10—10 of FIG. 9.

FIG. 14 is a side elevational view of a modification of the stapler of this invention in which a replaceable cartridge of staples is used.

FIG. 15 is a cross-sectional view of the stapler of FIG. 14 taken at line 15—15.

FIG. 16 is a side elevational view similar to that shown in FIG. 14 with the cartridge and anvil inserted and the cartridge holder advanced closer to the anvil holder, and with a partial cross-section of the cartridge and cartridge holder.

FIG. 17 is a side elevational view of a staples cartridge suitable for use in the stapler of FIGS. 14–16.

FIG. 18 is a top view of the cartridge of FIG. 17.

FIG. 19 is a rear elevational view of the cartridge of FIG. 17.

FIG. 20 is a cross-sectional view taken at line 20—20 of FIG. 18.

FIG. 21 is a cross-sectional view taken at line 21—21 of FIG. 18.

FIG. 22 is a cross-sectional view taken at line 22—22 of FIG. 18.

FIG. 39 is a forward elevational view of the end portion of the stapler shown in FIGS. 37 and 38 taken at line 39—39 of FIG. 38.

FIG. 40 is a cross-sectional view of the end portion of the stapler shown in FIGS. 37 and 38 taken at line 40—40 of FIG. 38.

FIG. 41 is a view similar to that shown in FIG. 39 except that the grooves in the anvil are adapted to receive staples arranged as in FIG. 34.

FIG. 42 is a view similar to that shown in FIG. 40 showing the end portions of staples arranged as in FIG. 34.

FIG. 43 is a side elevational view of a staples cartridge suitable for use in the end portion of the stapler of FIGS. 37 and 38.

FIG. 44 is a top view of the cartridge of FIG. 43.

FIG. 45 is a rear elevational view of the cartridge of FIG. 43.

FIG. 46 is a cross-sectional view taken at line 46—46 of FIG. 44.

FIG. 47 is a cross-sectional view taken at line 47—47 of FIG. 39.

Figure 13:
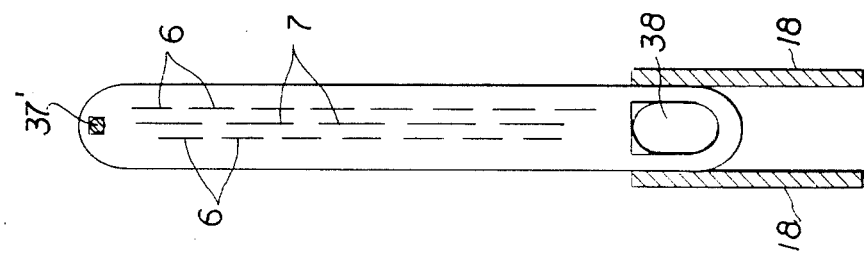
FIG. 13 is a cross-sectional view taken at line 13—13 showing the staples in the staple cartridge.

More specifically FIG. 1 shows a mesentery 1 which has the bowel 2 surrounding the greater portion thereof. The base or web 3 of the mesentery has large blood vessels 4 and smaller blood vessels 5 passing therethrough and into the larger part of the mesentery.

FIG. 2 shows the mesentery as shown in FIG. 1 in which the three rows of staples of this invention have been applied across the web 3 of the mesentery. There are two outer rows of smaller staples 6 with the staples in one row being staggered with those in the other row of small staples 6, preferably with very small space between adjacent staples so that the staples in one row overlap the staples in the other row. A third row of large staples 7 is positioned between the two rows of smaller staples. This arrangement insures that both the small and large blood vessels are blocked or sealed by this arrangement of staples. Complete blockage of the blood vessels across the width of the web is desirable when the complete bowel is to be removed.

FIG. 3 shows the mesentery in which half of the web has the blood vessels sealed by a horizontal arrangement of the three rows of staples (two rows of small and one row of large staples) and a similar vertical arrangement leading from the midpoint of the web upward to the bowel thereby sealing the blood vessels in that area and thereby accommodating the removal of the left half of the bowel. Lesser or larger portions of the bowel can be accommodated by appropriate changes in the positioning of the three rows of staples as described above.

While it is preferred to have the row of larger staples positioned between two staggered rows of smaller staples, it is also contemplated that the row of large staples may be positioned outside the two rows of smaller staples. Moreover it is also contemplated that, with the third row of large staples, it may be possible to effect adequate sealing of the blood vessels with the rows of small staples not staggered to each other. Nevertheless the inside positioning of the row of large staples and the staggering of the two rows of smaller staples are preferred for maximum efficiency of the sealing arrangement.

FIG. 4 shows a preferred shape of the grooves 8 in anvil 9 with the staple prongs 10 extending from the main portion 11 of the staple and extending toward anvil grooves 8.

FIG. 5 shows a preferred curved shape of the prongs 10 after the staple has been pressed against the anvil 9 and into the grooves 8. As previously stated, this curved shape of the prongs resembles stitching and reduces the pressure that might cut the tissue if uncurved or straight prongs are pressed against the main part 11 of the staple and pressure applied therebetween.

FIG. 6 shows a modification in which an additional or second row of the larger staple 7' is longitudinally spaced from the previously described three rows of staples and an incision 13 has been made between this additional row of larger staples and the said three rows. This extra row of staples is designed to prevent back bleeding.

FIG. 7 gives a front elevational view of a modification of the stapler 14 of this invention which in part resembles a gun with handle 15, barrel 16 and trigger 30. Safety guard 29 is shown in retracted position. Anvil 17 is supported by arm 18 extending from the forward or front end of barrel 16. Staple cartridge 19 is supported by cartridge holder 20. Prongs 10 of the staples are inside the cartridge 19 and are not visible in this view. Positioning rod 21 passes through an opening extending through cartridge holder 20 and also through guides 22 and 22. Knob 23 is fastened to the back end of rod 21 and may advance the forward end of rod 21 to the anvil by pushing knob 23 forward and may retract the rod 21 away from the anvil by pushing knob 23 backward. Cartridge 19 is connected by an arm (not shown here) extending inside barrel 16 and is connected indirectly to knob 24. Knob 24 is capable by a screw arrangement shown in FIG. 10 to advance and retract the cartridge and cartridge holder. Axial rotation in a clockwise direction advances the cartridge holder and cartridge toward the anvil and counterclockwise rotation retracts these away from the anvil. Gap setting 25 allows a measurement of the gap between the anvil and the staple cartridge.

FIG. 8 is a view of the stapler similar to that of FIG. 7 except that the positioning rod 21 has been pushed to a position closer to anvil 17 by forward advancement of knob 23. When the anvil and cartridge are positioned against the tissue to be stapled, further advancement of rod 21 will pierce the tissue by pointed end 21' which will eventually enter an opening (not shown here) in anvil 17 and thereby hold the tissue in position for the stapling operation. Trigger 30 is shown in open position, closing of trigger 30 toward handle 15 to the position shown in FIG. 7 actuates the forward movement of plunger 27 and plunger arm 32 (neither of which is shown in FIG. 8 but both are shown in FIG. 10) to force the staples into the grooves of the anvil. A partial cross-section of the staple cartridge 19 and cartridge holder 20 shows the staple prongs 10 and staple main portion (or leg) 11 and staple pushers 31 which are moved forward by pusher arm 32. Pusher arm 32 is actuated by plunger arm 27 which is pivotally connected by pin 26 (not shown in FIG. 8 but shown in FIG. 10) to trigger 30 which is pivotally connected by fulcrum pin 33. Before trigger 30 is activated, safety bar 29 is pushed back to its retracted position as shown in FIG. 7.

FIG. 9 is a top view of the stapler of FIG. 8 showing a partial cross-sectional view.

FIG. 10 is an elevational cross-sectional view taken at line 10—10 of FIG. 9. In FIGS. 9 and 10, plunger 27 is connected at one end to cartridge holder 20 and at the other end is pivotally connected to handle trigger 30 by means of pin 26. Trigger 30 is pivotally connected to the upper end of handle 15 by means of fulcrum pin 33. Safety bar 42 is shown in position to prevent premature or accidental movement of trigger 30. When knob 24 is rotated, it is held in position by collar 29 of outer shell 43 while the rotation causes advancement or retraction of screw 28 so that rotation of the threads 35 inside knob 24 in the grooves of screw 28 will cause the desired advancement or retraction of screw 28 which is fixed to base 36 which is fixed to both rod 27 and the top of handle 15. Thus the rotation of knob 24 causes handle 15 and likewise plunger 27, cartridge holder 20 and staple cartridge 19 to advance toward or retract from the anvil 17' in anvil holder 17. The lower edge of outer shell 43 is turned inwardly and horizontally and is slidably mounted in groove 44 in the upper part of handle 15 so that handle 15 can be moved relative to outer shell 43. When staple holder 19 has been positioned against the tissue to be stapled, the stapling action is activated by pressing or squeezing trigger 30. Rods 41 are fixed to outer shell 43 and extend all the way to arm 18 to which anvil 17 is attached.

Figure 11:
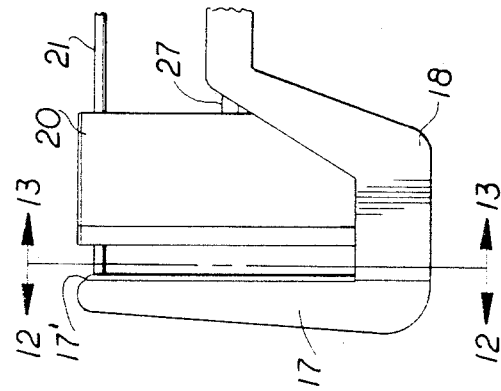
FIG. 11 is a partial side elevational view of the stapler of FIG. 8 with the positioning rod shown in its farthest position extending into an opening in the anvil holder with a partial cross-sectional view.

FIG. 11 is a view of the front part of the stapler of FIGS. 8 and 9 showing the cartridge and cartridge holder 20 in a position closer to the anvil 17' in anvil holder 17.

Figure 12:
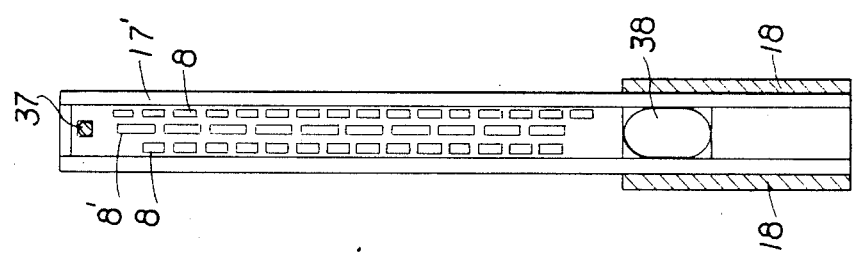
FIG. 12 is a cross-sectional view taken at line 12—12 showing the grooves in the anvil.

FIG. 12 is an elevational view of the anvil 17' taken at line 12—12 of FIG. 11. Grooves 8 and 8' are positioned to receive and turn the prongs of the respective staple prongs. Opening 37 is an opening in the anvil to receive the end of positioning pin 21. Guide bar 38 is fixed to the anvil holder 17 and is adapted to fit into an opening (not shown) in the cartridge holder.

FIG. 13 is an elevational view of the staple cartridge taken at line 13—13. Small staples 6 are in the outside rows and the staples in one row are staggered from the staples in the other row. Large staples 7 are in the middle row in between the two rows of small staggered staples 6. The dimensions of the respective parts of FIGS. 12 and 13 are not according to scale but are exaggerated to show relative positioning. Opening 37' is an opening in the cartridge to allow passage of positioning pin 21. Guide bar 38 fits into an opening in the cartridge holder and insures that the cartridge is correctly positioned with respect to the anvil.

In some cases, such as shown in FIGS. 7-11, the stapler has a staple cartridge as an integral part of the stapler, in which case the whole stapler is discarded once the staples have been applied to the patient. In other cases, such as in FIGS. 14-16, the stapler is adapted to receive replaceable staple cartridges in which case the stapler may be used repeatedly with new cartridges, with sterilization of the gun possible after each use if considered advisable. With the use of replaceable cartridge the anvil may be an integral part of the stapler or may be a replaceable anvil provided that the grooves in the anvil are registered so that each groove is positioned opposite to the prong which it is to bend. The replaceable anvil is fastened to the anvil holder by means of lips extending from the anvil which slip into slots or grooves in the anvil holder and hold the anvil in the desired registered position.

FIG. 14 is an elevational side view of a stapler 14' in which replaceable staple cartridges and anvils may be inserted. Anvil support arm 18' extends from the front end of barrel 16'. Cartridge holder 20' is attached to a shaft or plunger (not shown) positioned inside barrel 16'. Positioning pin 21' passes through an opening in cartridge holder 20' and may have its position adjusted by pushing or pulling knob 23'. The position of cartridge holder is adjusted by turning knob 24' which by an internal screw arrangement (not shown) advances or retracts the cartridge holder. Knob 24' is held in position by collar 40' while the screw device in the interior is turned to advance or retract the plunger arm. Trigger 30' is pivotally attached to a plunger arm (not shown) inside the barrel or sleeve 16' and by virtue of fulcrum pin 33' which gives leverage against handle 15' for the purpose of moving the plunger arm inside of barrel 16'. When knob 24' is rotated, it is prevented from moving axially by collar 40' but screw 28' is caused to move out of or into the interior of knob 24' by virtue of reciprocal threads (not shown) in the interior of knob 24'.

FIG. 15 is a cross-sectional view taken at line 15—15 of FIG. 14 showing the screw 28' advanced or retracted by the turning of knob 24' and thereby advancing or retracting plunger 27'.

FIG. 16 is another side elevational view of the stapler of FIG. 14 with a partial cross-sectional view of the cartridge holder 20' and of the cartridge 19' shown inside the cartridge holder with a row of staples 6'.

FIG. 17 is a side elevational view of a replaceable cartridge showing the first row of staples 6' in partial cross-sectional view, suitable for use in the stapler of FIGS. 14-16 showing plunger manifold arm 34''' and individual plungers 34''''. Staple holder 39' has the three rows of staples held in the interior thereof.

FIG. 18 is a top view of the staple cartridge of FIG. 17 showing manifold plunger 34''' and three rows 34'''', 34''''' and 34'''''' of individual plungers for the small staples, large staples and small staples respectively.

FIG. 19 is a rear view of the cartridge of FIG. 17.

FIG. 20 is a cross-sectional view taken at line 20—20 of FIG. 18 showing a row of the small staples 6'.

FIG. 21 is a cross-sectional view taken at line 21—21 of FIG. 18 showing the row of large staples 7'.

FIG. 22 is a cross-sectional view taken at line 22—22 of FIG. 18 showing a row of the small staples 6'.

Figures 23, 24:
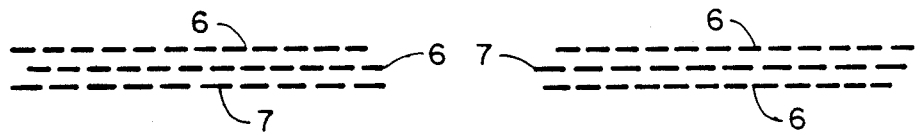
FIGS. 23–31 are top views of a variety of arrangements of rows of staples of small and large size which are suitable for the practice of this invention. Each staple is represented by a single line.

FIG. 23 is a top view showing an arrangement of two rows of small staples 6 and a third row of larger staples 7.

FIG. 24 is a top view showing an arrangement of three rows of staples, the first and third rows having staples of small size 6 and staggered with each other and a second or intermediate row of large size 7, as shown in FIGS. 2, 3, 12 and 13.

Figures 25, 26:
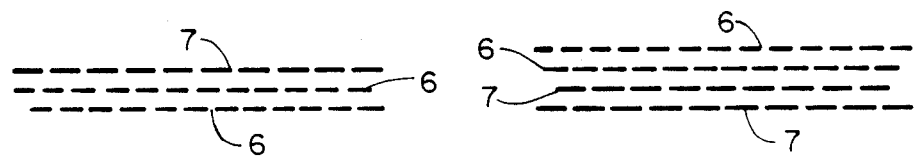

FIG. 25 is a top view of an arrangement of three rows of staples, the first row having staples of large size 7 and the second and third rows staggered with staples of small size 6.

FIG. 26 is a top view of an arrangesment having four rows of staples, the first two rows being of small staples 6 staggered in the respective rows and the second two rows or third and fourth rows of large staples 7 staggered in the respective rows.

Figures 27, 28:
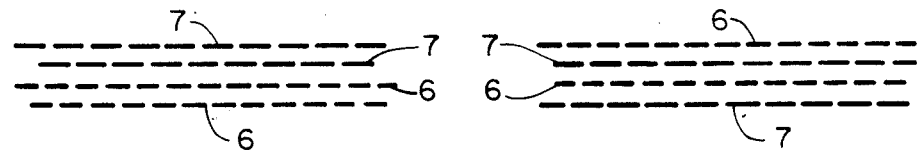

FIG. 27 is an arrangement of four rows of staples, the first two rows comprising large staples 7 staggered with each other, and the third and fourth rows comprise small staples 6 staggered with each other.

FIG. 28 is an arrangement of four rows of staples, the first and third rows comprising small staples 6 staggered with each other and the second and fourth rows comprising large staples 7 staggered with each other.

Figures 29, 30:
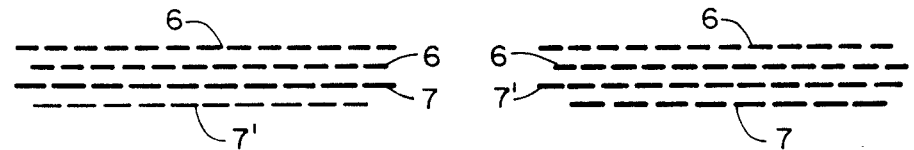

FIG. 29 is an arrangement of four rows of staples, the first and second rows comprising small staples 6 staggered with each other, the third row comprising large staples 7 and the fourth row comprising staples of an intermediate size 7'.

FIG. 30 is an arrangement of four rows of staples, the first two rows comprising small staples 6, staggered with each other, the third row comprising staples of an intermediate size 7', and the fourth row comprising large staples 7.

Figure 31:
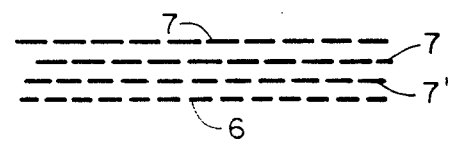

FIG. 31 is an arrangement of four rows of staples, the first two rows comprising large staples 7, staggered with each other, the third row comprising intermediate sized staples 7' and the fourth row comprising small staples 6.

In the preceding figures the effectiveness of the staples for sealing off the various sized blood vessels in the mesentery are dependent on using rows of staples in which the staples in a particular row are of identical size but there is at least one row in which the staples, although identical in size to the others in that row, are different in size from the staples in other rows. It has also been found that it is possible to seal off the various sized blood vessels in the mesentery and in the omentum by having carefully arranged staples alternating in size in the same row. In some cases the gap or space between the ends of a large and a small staple is covered or embraced by either a large staple or a small staple staggered in the adjacent parallel row of staples. In other cases the large staple may be large enough and arranged in the adjacent row opposite to and embracing the whole of the small staple and the two gaps adjacent to the small staple. In this way all the blood vessels are effectively sealed. A third row of alternately sized staples may be used although not necessary with the first and third rows of staples having the same terminal size of staple.

Accordingly the anvils used with these arrangements have grooves adapted to receive these staples in their particular arrangement and also the cartridges used have the staples in the desired arrangement and specifically correspond with the grooves in the anvil.

Figure 32:
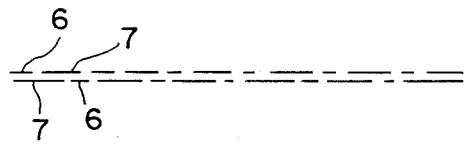
FIG. 32 is a top view of two rows of staples in which the staples are alternately of a small and of a large size.

FIG. 32 is an arrangement of two rows of staples in which small staples 6 and large staples 7 are alternately arranged in the same row. In this arrangement each staple is in a staggered arrangement opposite and embracing or overlapping the space between staples in the adjacent parallel row of staples.

Figure 33:
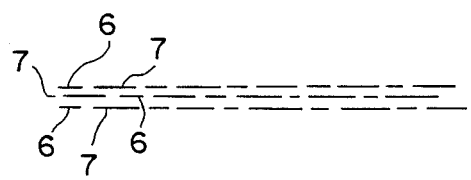
FIG. 33 is a top view of three rows of staples in which the staples are alternately of a small and of a large size.

FIG. 33 is a similar arrangement of staples as in FIG. 32 except that a third similar row is added so that the first and third rows are identically arranged.

Figure 34:
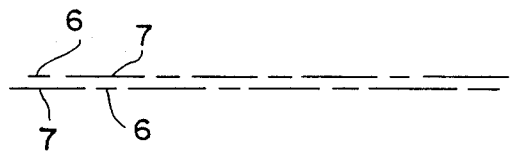
FIG. 34 is another arrangement of two rows of staples as in FIG. 32 in which the large staples are large enough to overlap the small staple and the two gaps adjacent to the small staple.

FIG. 34 is another arrangement of two rows of staples in which small staples 6 and large staples 7 are alternately arranged in the same row as in FIG. 32 except that the large staples are so much larger than the small staples that a large staple can be staggered and arranged opposite two gaps between staples and embracing or completely overlapping a small staple in the adjacent parallel row of staples.

Figure 35:
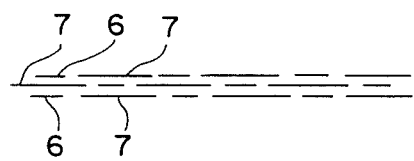
FIG. 35 is a similar arrangement as in FIG. 34 except that a third similar row of staples is added so that the first and third rows are identical.

FIG. 35 is a similar arrangement of staples as in FIG. 34 except that a third row is added so that the first and third rows are identically arranged.

Figure 36:
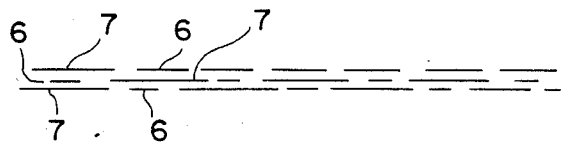
FIG. 36 is a somewhat similar arrangement of three rows of staples as in FIG. 35.

FIG. 36 is a similar arrangement of staples as in FIG. 35 except that the first and third rows in FIG. 36 start at the left side with a small staple 6 whereas in FIG. 35 the first and third rows start at the left side with a large staple 7.

Figure 37:
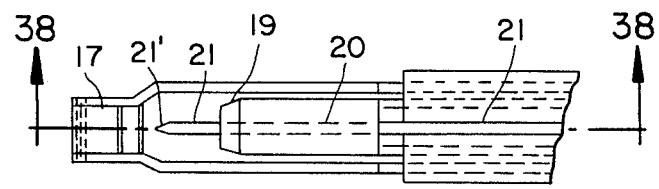
FIGS. 37 and 38 are the top and side cross-sectional view of the front end section of a stapler as shown in FIGS. 9 and 10 but adapted to deliver two rows of staples as depicted in FIG. 32.

FIG. 37 is a top view similar to that shown in FIG. 9 but for a stapler designed to staple two rows of staples in which each row of staples are of alternating size as shown in FIG. 32 (now arranged vertically instead of horizontally as in FIG. 32).

Figure 38:
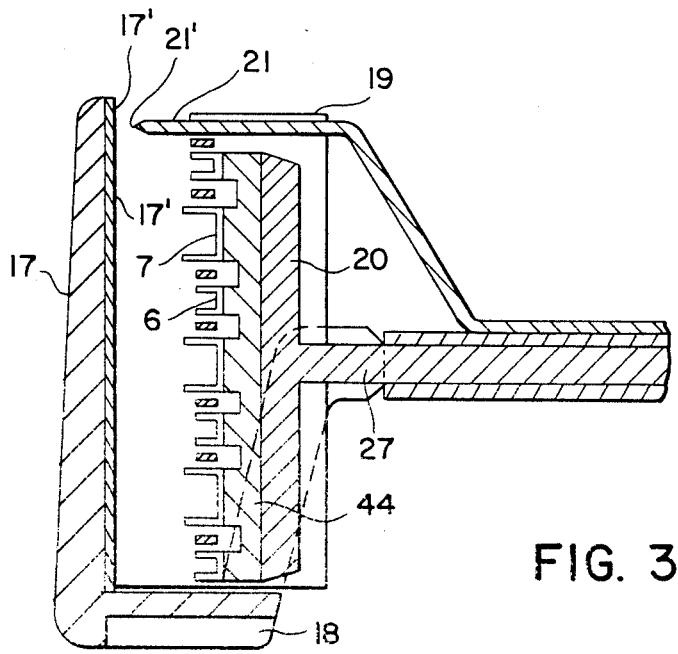

FIG. 38 is a side elevational cross-sectional view taken at line 38—38 of FIG. 37.

FIG. 39 is a forward elevational view taken at line 39—39 of FIG. 38.

FIG. 40 is a rearward elevational view taken at line 40—40 of FIG. 38.

FIG. 41 is a similar view to that shown in FIG. 39 except that the anvil grooves are adapted for use with staples arranged as in FIG. 34 (now arranged vertically instead of horizontally as shown in FIG. 34).

FIG. 42 is a similar view to that shown in FIG. 40 except that the staples are arranged as in FIG. 34 (now arranged vertically instead of horizontally as in FIG. 34).

FIG. 43 is a side elevational view of a replaceable cartridge showing the first row of alternating small staples 6 and large staples 7 in partial cross-sectional view, suitable for use in the stapler of FIGS. 14-16 modified as in FIGS. 37 and 38 showing plunger manifold arm 44 and individual plungers 45 for the small staples 6 and 46 for the large staples 7. Staple holder 47 has the two rows of staples held in the interior of cartridge 47.

FIG. 44 is a top view of the staple cartridge 47 of FIG. 43 showing manifold plunger 44 and two rows of alternating plungers 45 for the small staples 6 and plungers 46 for the large staples 7.

FIG. 45 is a rear view of the cartridge of FIG. 43.

FIG. 46 is a cross-sectional view taken at line 46—46 of FIG. 44 showing a row of the alternate small staples 6 and large staples 7.

FIG. 47 is a cross-sectional view taken at line 47—47 of FIG. 44 showing the row of alternating small staples 6 and large staples 7.

The views of staples, cartridges, etc., are not according to scale but are merely illustrative and may be out of proportion since it is difficult to depict exact proportions. Moreover the number of staples in a cartridge is also not representative and may vary considerably from those shown in the figures.

While the lengths of the prongs of the smaller and larger staples are not as critical as the lengths of the main portion of the respective staples, the prongs generally have lengths in the range of $\frac{1}{2}$ to 1 1/5 the length of the main portions of the respective staples. Thus the smaller staples advantageously have prong lengths of about 1.0 to 2.75 millimeters and the larger staples have prong lengths of about 1.5 to 4.5 millimeters in length. In fact the length of the prongs may vary slightly depending on the actual length of the main portion of the staple.

The distance between the first and third rows of staples is advantageously a maximum of about 6 millimeters and a minimum of about 3 millimeters, preferably this distance is about 4 millimeters, and the second row of staples is advantageously about midway between the first and third rows. When there is a fourth row of staples, the distance between the third and fourth rows is generally approximately the same as between the other adjacent rows.

The staples themselves may be made of any appropriate material that is capable of being bent in the manner described and has the strength to hold its shape once bent, provided the material does not produce an adverse effect on or cause infection of the tissue on which it is being used. Preferably the staples are of stainless steel of the same type as is presently being used in the vascular staples.

In applying the staples the stapler is positioned adjacent to the appropriate part of the mesentery or omentum with the jaws of the anvil and the staple cartridge on opposite sides of the tissue to be stapled. Then the pointed positioning rod 21 is pushed by means of knob 23 so that the tissue is pierced by this pointed rod and the end of rod 21 rests in opening 25 of the anvil so that the tissue is fixed in position with respect to the stapler. Then the cartridge 19 and cartridge holder 20 are advanced by axial rotation of knob 24 to a position where the cartridge is pressed against the tissue. Then the staples are applied to the tissue and bent into set shape by pressure actuated by the pressing of trigger 30. After the staples have been applied, the rod 21 is retracted by pressing backward on knob 23 and the stapler is removed.

The stapler and cartridges shown in the drawings are specified to three rows of staples. Obvious modifications can be made to staples and cartridges to provide the various arrangements of staples shown in FIGS. 23-31 and the anvils in the stapler will be modified to receive and bend the prongs of the respective sizes and positions of the staples being applied.

In some cases where the new staplers of this invention are not available, it is possible to effect desired arrangements with staplers designed for double rows of staples. For example in providing the arrangements of FIGS. 26 and 27, the staples may be applied as two double rows of small and large staples by using one stapler to apply one double row of staples of one size and another stapler to apply a second double row of a different size of staples.

Where it is desired to effect arrangements of FIGS. 23 and 25, the staples may be applied by one stapler to give one double row of one size of staple, and another stapler is used in which one row of staples is removed so as to provide a single row of staples different in size from the double row.

Also where the single row of staples of different size is between the two rows of staples of the same size as in FIGS. 24, 26 and 31, two or three double staplers may be used with one row of staples removed in each so that each stapler will deliver a single row of staples at one time.

The following examples illustrate how staplers used for applying two rows of staples of the same size may be used for applying two rows of staples of one size and then another stapler used for applying one or two rows of a different sized staple. These examples also illustrate the ineffectiveness of three rows of staples of the same size and the effectiveness of three rows or four rows of staples where one or two of the rows of staples are of a different size from the other two rows.

In the examples given below two staplers are used described as "Proximate Reloadable Linear Stapler" manufactured by Ethicon, Inc. One affixes a double row of staggered staples each having a size of 3.0 mm×2.5 mm before closure and the other affixes a double row of staggered staples each having a size of 4.0 mm×4.5 mm before closure. The first dimension in each case is for the main part of the staple and the second dimension is for each of the two prongs.

EXAMPLE I

In an operation on the mesentery of a patient, the surgeon affixes two parallel rows of the smaller staples described above. Upon cutting the mesentery distal to the stapled lines, there is profuse bleeding requiring clamping and ligation in the traditional manner to effectively stop the blood flow. This procedure is repeated in three subsequent operations on the mesentery with similar results in each case.

EXAMPLE II

In another operation on a patient for whom a part of the bowel and adjoining part of the bowel are to be removed, the surgeon carefully affixes by means of the second of the above staplers two parallel staggered rows of the larger size of staples. When an incision is made across the area of the mesentery to be resected distal to the staple lines and after removal of the bowel and mesentery sections, the incision is inspected for leakage. It is found that there is profuse blood leakage and it is necessary to clamp the blood vessels individually and to ligate them in the traditional manner to stop the flow of blood.

EXAMPLE III

In an operation upon a patient for whom a part of a bowel and adjoining mesentery are to be removed, the surgeon carefully affixes across the mesentery two parallel rows of the larger staples described above. Then one of the rows of staples is removed from the cartridge or cartridges used in the same stapler so that that stapler affixes only one row of such staples. By this method a third staggered row of the same sized staples is fixed substantially parallel to the first two rows across the mesentery. An incision is made across the area of the mesentery to be resected distal to the staple lines. After the sections of the mesentery are removed, the stapled area is carefully inspected to determine if the incision is properly sealed. It is found that there is profuse blood leakage and that the incision is not sealed within the recognized standard of medical care. It is then necessary to clamp the bleeding blood vessels individually and to ligate them in a traditional manner to stop the flow of blood.

EXAMPLE IV

In an operation upon a patient for whom a part of the bowel and adjoining mesentery are to be removed, the surgeon carefully affixes across the mesentery two parallel staggered rows of the larger staples as above described and then in close proximity and substantially parallel to these first rows two additional staggered rows of the smaller staples are affixed as described above for a total of four rows across the mesentery. After the incision is made distal to the four parallel lines of staples and the sections of bowel and mesentery are removed, the stapled incision is inspected for blood leakage. It is determined that there is no blood leakage and the incision is properly sealed within the recognized standard of medical care.

EXAMPLE V

In an operation upon a patient for whom part of the bowel and adjoining mesentery are to be removed, the surgeon carefully affixes across the mesentery first two parallel, staggered rows of the smaller staples as described above and then in very close proximity and substantially parallel to these first two rows a third of the larger staples as described above a total of three rows of staples across the mesentery. Then after an incision is made distal to the three lines of staples and removal of the sections of mesentery and bowel, inspection is made of the stapled incision and it is found that the incision is properly sealed within the recognized standard of medical care.

While these combinations are possible with the use of double staplers and alterations of the same, it is preferred to use the new staplers of this invention in which the desired three or four row arrangement of staples is effected simultaneously. Variations can be made in the design of the cartridges and the corresponding anvils. Variations can be made in the design of the cartridges and the corresponding anvils. Variations can be effected in the same three row stapler by the use of replaceable cartridges and anvils. Likewise variations are also possible for the same four row stapler by the use of replaceable cartridges and anvils.

In the drawings the staples are generally represented with heavy lines instead of in outline form and sometimes in order to avoid confusion background material has been omitted.

In the stapler of this invention it is important that the edges, particularly on the front of the stapler, should be well rounded to avoid tearing the tissue with which it may come into contact.

In summary, for use in the stapler, in the cartridge and in the process of this invention, the staples used should have their dimension in the middle or main portion, that is the portion connecting the two prongs, advantageously in the range of 2.5 to 4.5 millimeters, preferably with the smaller staples having this dimension in the range of 2.5 to 3.5 millimeters and the larger staples having this dimension in the range of 3.5 to 4.5 millimeters, the larger staples preferably being at least 30 percent longer in this dimension than the smaller staples.

In the process and staplers using rows of staples having alternating smaller and larger sizes the smaller staples may have a size as small as 2.5 millimeters and the larger staple may have a length as great as 6 millimeters, preferably as large as 45-5 millimeters. The gaps or distances between adjacent staples in a particular row are the same as used in present day practice.

In the arrangement shown in FIGS. 37 and 38 the operation of the complete stapler is the same as for the stapler shown in and described for FIGS. 9 and 10. Plunger arm 27 advances cartridge holder 20 and causes staple cartridge 19 to advance toward or retract from anvil 17' in anvil holder 17. In identical manner the stapling action is activated by squeezing trigger 30 (shown in FIG. 10).

Also in summary the alternating type of arrangement of staples may be defined as having two adjacent parallel rows of staples with the staples in each row alternating in size, with the staples in one row staggered with the staples in the other adjacent row, the smaller sized staples being long enough to bridge the gap between staples and to overlap at least a portion of the two adjacent staples and the larger sized staples having a length in the range of at least 30 percent larger than said smaller staples and up to a length sufficient to overlap the entire length of the smaller staple plus the two adjacent gaps between staples and at least a portion of each of the adjacent longer staples in the adjacent parallel row of staples.

While certain features of this invention have been described in detail with respect to various embodiments thereof, it will of course be apparent that other modifications can be made within the spirit and scope of this invention, and it is not intended to limit the invention to the exact details insofar as they are defined in the following claims.

The invention claimed is:

1. A process for preparing a mesentery of the abdomen for subsequent removal of at least a portion of the bowel comprising the step of preventing the flow of blood from blood vessels leading to the section of the bowel to be removed comprising the step of applying staples across at least a portion of the web of the mesentery, said staples comprising an arrangement of staples of different sizes selected from the group consisting of:
   (a) two adjacent parallel rows of staples having the staples in each row alternating in size, with the staples in one row staggered with the staples in the other adjacent row, the smaller sized staples being long enough to bridge the gap between staples and to overlap at least a portion of the two adjacent staples and the larger sized staples having a length in the range of at least 30 percent larger than said smaller staples and up to a length sufficient to overlap the entire length of the smaller staple plus the two adjacent gaps between staples and at least a portion of each of the adjacent longer staples in the adjacent parallel row of staples, and
   (b) two parallel rows of identically sized staples, the staples in one of said rows being staggered with the staples in the other row, and also a third row of staples parallel to said first two rows of staples and having a dimension in the main portion thereof different from the dimension of the main portion of the staples in said first two rows, there being at least 30 percent difference in said dimension sizes, in which said three rows of staples the middle row of staples is positioned approximately equidistant between the other two rows of staples.

2. The process of claim 1 in which said arrangement of staples comprises two parallel rows of identically sized staples, the staples in one of said rows being staggered with the staples in the other row, and also a third row of staples parallel to said first two rows of staples and having a dimension in the main portion thereof different from the dimension of the main portion of the staples in said first two rows, there being at least 30 percent difference in said dimension sizes, in which said three rows of staples the middle row of staples is positioned approximately equidistant between the other two rows of staples.

3. The process of claim 2 in which said third parallel row of staples is positioned between said first two rows of staples.

4. The process of claim 3 in which the staples in the said first two parallel rows of staples have a main body dimension in the range of 2.5-3.5 millimeters and the staples in the said third parallel row of staples have the main body dimension of 3.5-4.5 millimeters, the said dimension of the larger staples being at least 30 percent larger than the said dimension of the smaller staples.

5. The process of claim 4 in which said smaller staples have said dimension of approximately 3 millimeters and said larger staples have said dimension of approximately 4 millimeters.

6. The process of claim 2 in which said third row of staples is positioned outside the said first two rows of staples.

7. The process of claim 6 in which the staples in the first two parallel rows have a main body dimension of 2.5–3.5 millimeters and the main body dimension of the staples in the third row is 3.5–4.5 millimeters, the dimension of said larger staples being at least 30 percent larger than the dimension of said smaller staples.

8. The process of claim 7 in which said smaller staples have said dimension of approximately 3 millimeters and said larger staples have said dimension of approximately 4 millimeters.

9. The process of claim 2 in which the said three parallel rows of staples is extended fully across said web.

10. The process of claim 2 in which the said three rows of staples extend only partially across said web and then extend toward the bowel to the point where said bowel removel will terminate.

11. The process of claim 2 in which there is a fourth row of said staples positioned parallel to said two parallel rows of staples and spaced substantially from the adjacent of said rows of staples a distance approximately equal to the distance between said other adjacent rows.

12. The process of claim 11 in which the first and second rows of staples are of smaller sized staples and the third and fourth rows are of larger sized staples.

13. The process of claim 12 in which the respective rows of staples are positioned by two separate staplers, one capable of delivering double rows of said smaller sized staples and the other capable of delivering double rows of said larger sized staples.

14. The process of claim 11 in which the first and second rows of staples are of larger sized staples and the third and fourth rows are of smaller sized staples.

15. The process of claim 14 in which the respective rows of staples are positioned by two separate staplers, one capable of delivering double rows of said smaller sized staples and the other capable of delivering double rows of said larger sized staples.

16. The process of claim 2 in which there is applied a fourth row of identically sized staples, said fourth row of staples being positioned parallel to said other three rows of staples and spaced from the adjacent of said three rows a distance approximately equal to the distance between other adjacent rows of said three rows of staples.

17. The process of claim 16 in which the first two rows of staples have a main body dimension in the range of 2.5–3.5 millimeters and the third and fourth rows have a main body dimension in the range of 3.5–4.5 millimeters, the said dimension in the larger staples being at least 30 percent larger than the said dimension in said smaller staples.

18. The process of claim 17 in which the smaller staples have said dimension of approximately 3 millimeters and the larger staples have said dimension of about 4 millimeters.

19. The process of claim 16 in which the first two rows of staples have a main body dimension in the range of 3.5–4.5 millimeters and the third and fourth rows have a main body dimension in the range of 2.5–3.5 millimeters, the said dimension in the larger staples being at least 30 percent larger than the said dimension in the smaller staples.

20. The process of claim 19 in which the smaller staples have said dimension of approximately 3 millimeters and the larger staples have said dimension of about 4 millimeters.

21. The process of claim 2 in which the respective rows of staples are positioned by two separate staplers, one capable of delivering a double row of one size of staples and the other capable of delivering a single row of a different size of staple.

22. The process of claim 2 in which the distance between the first and third rows of staples is 3–6 millimeters.

23. The process of claim 1 in which said arrangement of staples comprises two adjacent parallel rows of staples having the staples in each row alternating in size with the staples in one row staggered with the staples in the other adjacent row, the smaller sized staples being long enough to bridge the gap between staples and to overlap at least a portion of the two adjacent staples in the adjacent row and the larger staples having a length in the range of at least 30 percent larger than said smaller staples and up to a length sufficient to overlap the entire length of the smaller staple plus the two adjacent gaps between staples and at least a portion of each of the adjacent longer staples in the adjacent parallel row of staples.

24. The process of claim 23 in which said arrangement also contains a third row of staples also alternately arranged, the first staple in the said third row being identical in size to the first staple in the first row of said arrangement.

25. In a stapling device designed for use on a patient which comprises:
 (a) a handle by which the device may be held in the operator's hand;
 (b) a sleeve having a forward and a rear end thereto, which sleeve is connected at a point near its rear end to said handle at an angle of about 90°–100°, at which point said handle is slidably mounted at the interior of said sleeve, and said sleeve having a knob extending from the rear end thereof;
 (c) a shaft extending lengthwise and inside said sleeve and being connected at one end to said handle adjacent to the area where said handle is slidably mounted on said sleeve;
 (d) an adjusting means for advancing said shaft toward the forward end of said sleeve and for retracting said shaft toward the rear end of said sleeve, said adjustment being effected by the axial rotation of said knob extending from the rear end of said sleeve;
 (e) a cartridge holding means attached to and positioned perpendicularly from the opposite end of said shaft from the end connected to said handle, said cartridge holding means being capable of being advanced and retracted with said shaft movement;
 (f) a support means extending downward and forward from the front end of said sleeve;
 (g) an anvil held by said support means in a position parallel to and opposite to said cartridge holding means;
 the improvement whereby said stapler device is suitable for use on a patient's mesentery which comprises:
 (h) a cartridge positioned on said cartridge holding means having two adjacent parallel rows of staples having the staples in each row alternating in size, with the staples in one row staggered with the staples in the other adjacent row, the smaller sized staples being long enough to bridge the gap between staples and to overlap at least a portion of the two adjacent staples in the adjacent row and the larger staples having a length in the range of at least 30 percent larger than said smaller staples and up to a length sufficient to overlap the entire length of the smaller staple plus the two adjacent gaps between staples and at least a portion of each of the adjacent longer staples in the adjacent parallel row of staples.

26. The stapling device of claim 25 in which said cartridge holding means also has a third adjacent parallel row of staples also alternately arranged, the first staple in the said third row being identical in size to the first staple in the first row of said arrangement, and said anvil having grooves therein spaced from and positioned opposite to and facing the prongs of the staples in said third row and positioned to receive and to turn the prongs of each said staple toward each other and toward the main part of said staple.

27. The stapling device of claim 25 in which the smaller staples of said rows of staples are long enough to bridge the gap between staples and to overlap at least a portion of each of the two adjacent staples to said gap in said adjacent row of staples.

28. The stapling device of claim 25 in which the larger staples of said rows of staples are long enough to overlap the entire length of the smaller staple plus the two adjacent gaps between staples and at least a portion of each of the adjacent longer staples in the adjacent parallel row of staples.

* * * * *